US00PP19582P3

(12) United States Plant Patent
Davidson

(10) Patent No.: US PP19,582 P3
(45) Date of Patent: Dec. 16, 2008

(54) ***MONARDA* PLANT NAMED 'ACHALL'**

(50) Latin Name: *Monarda disyma*
Varietal Denomination: AChall

(75) Inventor: Campbell G. Davidson, Ottawa (CA)

(73) Assignee: Her Majesty The Queen In Right of Canada as represented by the Minister of Agriculture and Agri-Food (CA)

( * ) Notice: Subject to any disclaimer, the term of this patent is extended or adjusted under 35 U.S.C. 154(b) by 106 days.

(21) Appl. No.: 11/648,951

(22) Filed: Jan. 3, 2007

(65) Prior Publication Data

US 2008/0184449 P1 Jul. 31, 2008

(51) Int. Cl.
*A01H 5/00* (2006.01)

(52) U.S. Cl. ..... Plt./455

(58) Field of Classification Search ..... Plt./455
See application file for complete search history.

(56) References Cited

U.S. PATENT DOCUMENTS

PP10,784 P * 2/1999 Collicutt et al. ..... Plt./455
PP16,741 P3 * 6/2006 Davidson ..... Plt./455

* cited by examiner

*Primary Examiner*—Wendy C. Haas
(74) *Attorney, Agent, or Firm*—Penny J. Aguirre

(57) ABSTRACT

A new cultivar of bee balm, *Monarda didyma* 'AChall', that is characterized by its deep red-purple blossoms that are present abundantly in June through August. The new variety is mid sized in height with an upright oval plant habit, is hardy in U.S.D.A. Zones 3 to 8, and exhibits dark green semi-glossy foliage that has shown resistant to powdery mildew.

2 Drawing Sheets

Botanical classification: *Monarda didyma.*
Variety denomination: 'AChall'.

BACKGROUND OF THE INVENTION

The present invention relates to a new and distinct cultivar of *Monarda didyma.* The new cultivar will be referred to hereafter by its cultivar name, 'AChall'. 'AChall' is a new variety of bee balm suitable for landscape plantings.

The new cultivar of Monarda was a selection from an on going breeding program involving open pollinated and controlled crosses at a research station in Morden, Manitoba, Canada. The inventor was selected 'AChall' as a single unique seedling in 2001, designated as accession no. 99-21, from seed collected and sown in 1999 that was derived from open pollination of, unnamed proprietary seedlings of *Monarda didyma.*

The new cultivar was asexually propagated by softwood cuttings and rhizome division in Morden, Manitoba, Canada. Asexual propagation in Morden, Manitoba, Canada and St. Paul, Minn. by these techniques have determined that the characteristics of this cultivar are stable and are reproduced true to type in successive generations.

SUMMARY OF THE INVENTION

The following traits have been repeatedly observed and represent the characteristics of the new *Monarda* as observed for a period of three years in Morden, Manitoba, Canada and St. Paul, Minn. These attributes in combination distinguish 'AChall' as a unique cultivar of *Monarda.*

1. 'AChall' exhibits deep red-purple blossoms.
2. 'AChall' blooms abundantly in June through August.
3. 'AChall' exhibits dark green, semi-glossy foliage.

4. 'AChall' is mid-sized in height (somewhat dwarf) and exhibits an upright and oval plant habit.
5. 'AChall' has shown good resistance to powdery mildew (*Sphaerotheca pannosa* var. *rosa*) under the conditions tested.
6. 'AChall' is hardy in U.S.D.A. Zones 3 to 8.

The new cultivar of *Monarda* can be readily distinguished from other cultivars. *Monarda* 'Petite Delight' (U.S. Plant Pat. No. 10,784) and *Monarda didyma* 'Coral Reef' (U.S. Plant Pat. No. 16,741) are the closest comparison cultivars known to the inventor. They are both similar to 'AChall' in flower color, however 'Petite Delight' has flowers that are more purple in color and a mounded plant habit while 'Coral Reef' has flowers that are more red in color and plants of 'Coral Reef' are much taller in height.

BRIEF DESCRIPTION OF THE DRAWING

The accompanying colored photographs illustrate the overall appearance and distinct characteristics of the new *Monarda,* 'AChall', as grown outdoors in a trial plots in St. Paul, Minn. The plants were approximately two years in age and the photographs were taken in mid summer of 2005.

Figure 1:
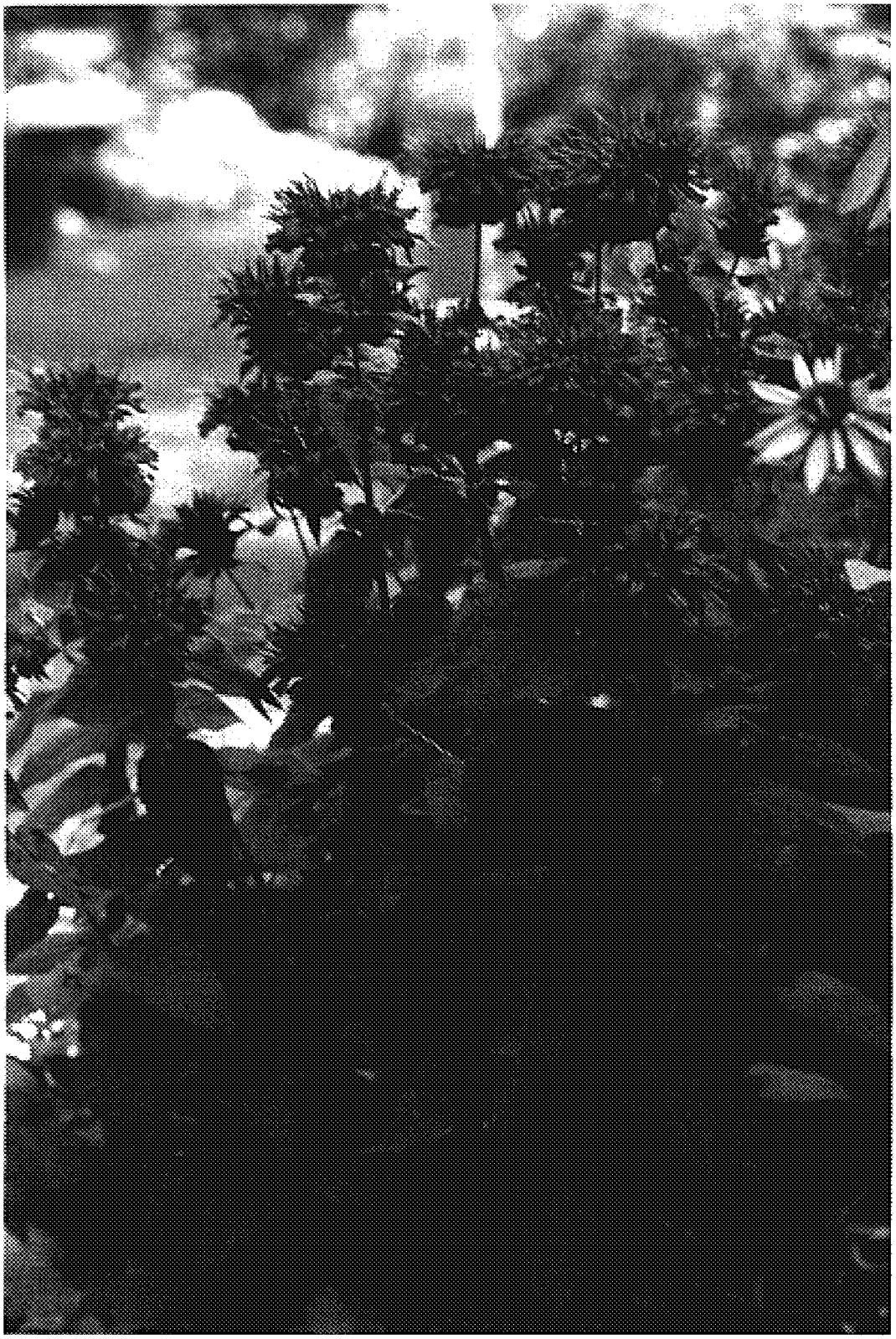
FIG. 1 provides a view of a plant of 'AChall' in bloom.
Figure 2:
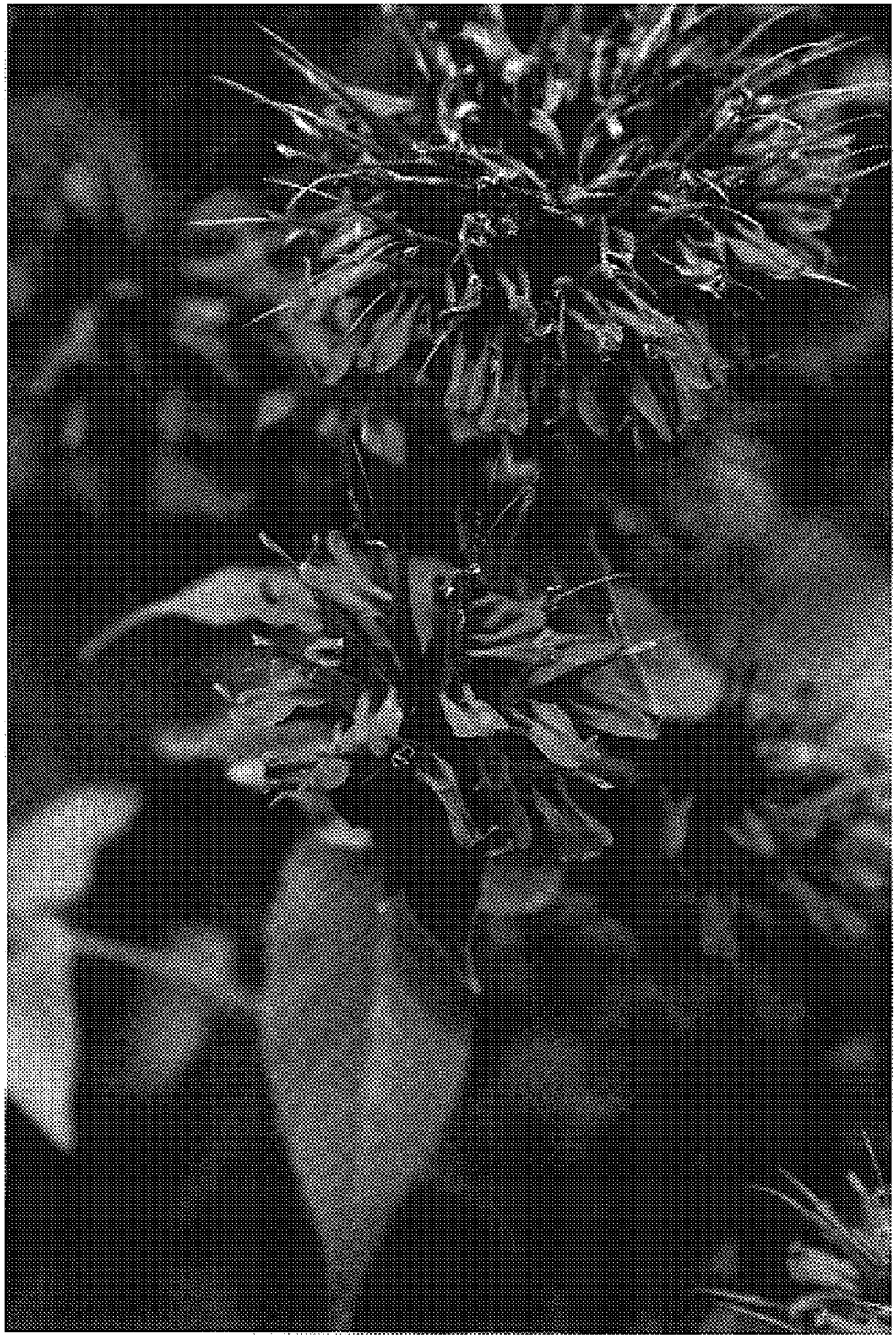
FIG. 2 provides a close-up view of flowers of 'AChall'.

The colors in the photographs are as close as possible with digital photography techniques available, the color values cited in the detailed botanical description accurately describe the colors of the *Monarda.*

DETAILED BOTANICAL DESCRIPTION

The following is a detailed description of the new cultivar as observed for three years as grown outdoors under field conditions in Morden, Manitoba, Canada and St. Paul, Minn.

The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Botanical classification*—*Monarda didyma* 'AChall'.

*Parentage.*—Proprietary, unnamed selections of *Monarda didyma* produced by open pollination.

*Blooming habit.*—Abundantly in June through August, can be prolonged and more dense with deadheading and pruning.

*Plant habit.*—Upright and oval-shaped.

*Height and spread.*—Mid-sized in height (somewhat dwarf), reaches about 35 to 45 cm in height and 45 to 55 cm in spread.

*Cold hardiness.*—U.S.D.A. Zone 3 to 8.

*Diseases and pests.*—Good degree of resistance observed to powdery mildew (*Sphaerotheca pannosa* var. *rosa*), no insect problems observed.

*Propagation.*—Softwood stem cuttings or by rhizome division.

*Growth.* —Vigorous and strong.

Branch description:

*Stem shape.*—Square.

*Stem color.*—Young; 146D, mature wood; 147C with highlights of 181A, particularly around nodes.

*Stem surface.*—Pubescent when young, becomes woody as it matures.

*Lateral branches.*—Average of 4 per main stem, average of 11.8 cm in length in the middle and 6.7 cm in length on the top 15 cm of the branch, average of 2.65 cm in diameter, average internode length of 4.3 cm.

Foliage description:

*Leaves.*—Opposite arrangement, ovate to ovate-lanceolate in shape, rounded to cordate base, acuminate apex, serrulate margins, semi-glossy texture on upper surface and lower surface, average of 75 cm in length and 45 cm in width, color young foliage upper surface; color between 137A and 137B, young foliage lower surface; color between 146A and 146B, mature foliage upper surface; 147A, mature foliage lower surface; a color between 146A and 147B.

*Petioles.*—Average of 1 cm in length and 5 mm in diameter, color of upper surface 147B with 185B on lateral edges, color of lower surface 147B, glabrous surface.

Inflorescence description:

*Inflorescence type.*—Borne terminally in whorls or as verticillaster.

*Inflorescence number.*—1 per lateral stem.

*Inflorescence fragrance.*—Pungent mint.

*Inflorescence size.*—Average of 5.5 cm in depth and 3.5 cm in diameter.

*Peduncles.*—Average of 7.8 cm in length and 6 mm in diameter, surface is glabrous, color is 137C with highlights of 184D.

*Bracts.*—About 9 per verticillaster, average of 3.6 cm in length and 2.3 cm in width, ovate to lanceolate in shape, surface is semi-glossy, color of upper surface is 185A with 144B towards margin and apex, color of lower surface is 185C and 185D with 143C and 143D towards margin and apex.

*Flower buds.*—Elongated tube in shape, average of 4.1 cm in length and 3 mm in width prior to opening, color is close to 60A suffused with 61A at terminal, surface is glabrous.

*Flower longevity.*—About 5 to 7 days, depending on temperature.

*Flower type.*—Tubular.

*Flower size.*—Average of 4.2 mm in diameter and 4.5 cm in depth.

*Sepals.*—Typically 13 per verticillaster, lanceolate in shape, margin is entire, color of upper surface prior to bloom; 144B suffused with 185B on margin and apex and base, color of lower surface prior to bloom; 145A suffused with 185B on margin, apex and base, opening flowers upper surface; 146A blended with 146B and 146C towards base and 187C and 187D blended at apex and margin, opening flowers lower surface; 146B blended with 146C and 146D towards base and 187C and 187D blended at apex and margin, fully open flowers upper surface; 148A blended with 59A and 187A, fully open flowers lower surface; 148A blended with 59A and 187A but less purple than upper surface, upper surface and lower surface is glabrous, average of 2.8 cm in length and 3.7 cm in width, apex is acuminate, base is rounded.

*Petals.*—2, the upper (lip) is hooded and erect and the lower is 3 lobed and more spreading, color: opening flowers upper surface; between 64A and 71B with the main tube 61A, opening flowers lower surface; 61A, fully open flowers upper surface; 64A with main tube 61A, fully open flowers lower surface; 72A with main tube 61A.

*Pistils.*—1, stigma is an average of 3.4 mm in length, an average of 1 mm in width, style is an average of 2.2 cm in length and 36D in color with 155A on exerted portion outside of flower, ovary is very small containing one ovule.

*Stamens.*—Typically 2, filaments are about 2.1 cm in length and 11D in color, anthers are an average of 3.8 mm in length, an average of 1.2 mm in width and 53B in color, pollen is scarce and 17D in color.

*Seeds.*—1 per flower, average of 1.4 mm in length and 0.8 mm in width, oval to rice shaped, color is 199B.

I claim:

1. A new and distinct cultivar of *Monarda* plant named 'AChall' as herein illustrated and described.

* * * * *